(12) United States Patent
Chou et al.

(10) Patent No.: US 10,429,174 B2
(45) Date of Patent: Oct. 1, 2019

(54) SINGLE WAVELENGTH REFLECTION FOR LEADFRAME BRIGHTNESS MEASUREMENT

(71) Applicant: TEXAS INSTRUMENTS INCORPORATED, Dallas, TX (US)

(72) Inventors: Hung-Yu Chou, Taipei (TW); Chien-Hao Wang, Taipei (TW); Tse-Tsun Chiu, New Taipei (TW); Fu-Kang Lee, New Taipei (TW); Liang-Kang Su, Tainan (TW)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 15/848,157

(22) Filed: Dec. 20, 2017

(65) Prior Publication Data

US 2019/0186897 A1 Jun. 20, 2019

(51) Int. Cl.
*G01B 11/06* (2006.01)
*G01B 11/30* (2006.01)
*G01B 11/28* (2006.01)
*G01B 11/16* (2006.01)

(52) U.S. Cl.
CPC ........ *G01B 11/0625* (2013.01); *G01B 11/162* (2013.01); *G01B 11/285* (2013.01); *G01B 11/303* (2013.01)

(58) Field of Classification Search
CPC . G01B 11/0625; G01B 11/162; G01B 11/285; G01B 11/303
USPC .................................................. 257/666–677
See application file for complete search history.

(56) References Cited

U.S. PATENT DOCUMENTS 8,604,436 B1 * 12/2013 Patel ....................... H01L 25/50
250/338.1

* cited by examiner

*Primary Examiner* — Tri T Ton
(74) *Attorney, Agent, or Firm* — Ronald O. Neerings; Charles A. Brill; Frank D. Cimino (57) ABSTRACT

A method for evaluating a leadframe surface includes positioning a leadframe on a measurement apparatus at a first predetermined distance relative to an end portion of a light source of an optical sensor; irradiating a predetermined area on a surface of the leadframe with light having a single predetermined wavelength from the light source; receiving, with a light receiver of the optical sensor, reflected light from the predetermined area on the surface of the leadframe, and converting the reflected light into an electric signal; determining a reflection intensity value of the predetermined area on the surface of the leadframe based on the electric signal; and calculating a reflection ratio of the predetermined area on the surface of the leadframe based on the reflection intensity value and a predetermined reference reflection intensity value associated with the light source.

27 Claims, 5 Drawing Sheets

SINGLE WAVELENGTH REFLECTION FOR LEADFRAME BRIGHTNESS MEASUREMENT

BACKGROUND

Leadframes are used in most integrated circuit packages. Most kinds of integrated circuit packages are made by placing a silicon chip on a leadframe, then wire bonding the chip to the metal leads of the leadframe, and then covering the bonded structure with plastic, usually an epoxy-based thermoset compound. A leadframe is essentially a thin layer of metal that connects the wiring from tiny electrical terminals on the semiconductor chip surface to the large-scale circuitry on electrical devices and circuit boards. Most leadframes are typically produced on a single, thin sheet of metal by stamping or etching to allow them to be quickly processed on the assembly line.

Prior to incorporating the leadframe in the integrated circuit package, a surface of the leadframe may be subject to various processes including plating and/or roughening to enhance adhesion between the leadframe and the epoxy during the packaging process. For example, the leadframe surface may be roughened by treating the leadframe with a chemical etchant. Further, the leadframe surface may be plated with a noble metal or metal alloy. These processes may be designed with the goal of reducing the tendency of the leadframe and plastic epoxy to separate as a result of differing thermal-expansion rates between the metal of the leadframe and the plastic of the package following prolonged exposure to moisture.

Although roughening and plating the leadframe surface may enhance adhesion properties of the leadframe, it may also affect the color and reflectivity (brightness or glossiness) of the leadframe surface. Further, due to process variations like current density, chemical concentration, equipment standards and the like during the leadframe plating and roughening processes, it may be difficult to precisely control the color and reflectivity of the surface of the leadframes from one batch to the next, thereby creating color and brightness inconsistencies of the leadframe surface. Still further, such color and brightness (reflection) variations may be difficult to quantify and standardize.

Consistency of the color and brightness of the leadframe surface may be important in a package production line that heavily relies on pattern recognition. More specifically, in the package production line, machines for performing a variety of processes including dispensing epoxy on top of the leadframe surface, die bonding, wire bonding, mount process, molding treatment, strip test process and the like may rely on pattern recognition. For example, in the mount process on the package production line, a machine may perform pattern recognition based on color and brightness of the leadframe surface to determine epoxy volume or epoxy shape dispensed on a leadframe surface. Even if there is a slight variation in the color and/or brightness of the leadframe surface, the machine may not accurately distinguish the leadframe surface from the epoxy and as a result, the pattern recognition process may fail or be performed incorrectly, thereby resulting in a significant loss of productivity and increase in cost on the assembly line.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one example, a method for evaluating a leadframe surface includes: positioning a leadframe on a measurement apparatus at a first predetermined distance relative to a distal end portion of a light source of an optical sensor; irradiating a predetermined area on a surface of the leadframe with light having a single predetermined wavelength from the light source; receiving, with a light receiver of the optical sensor, reflected light from the predetermined area on the surface of the leadframe, the light receiver photoelectrically converting the reflected light into an electric signal; determining a reflection intensity value of the predetermined area on the surface of the leadframe based on the electric signal from the light receiver; and calculating a reflection ratio of the predetermined area on the surface of the leadframe based on the reflection intensity value and a predetermined reference reflection intensity value associated with the light source.

In another example, a leadframe surface measurement system includes: memory; at least one processor that is coupled to the memory; an optical sensor including a light source and a light receiver; a measurement stage on which a leadframe is mountable, wherein the measurement stage is movable in three orthogonal axis directions relative to a measurement apparatus base to position the leadframe at a first predetermined distance relative to a distal end portion of the light source of the optical sensor, wherein the light source is configured to irradiate a predetermined area on a surface of the leadframe with light having a single predetermined wavelength, and wherein the light receiver is configured to receive reflected light from the predetermined area on the surface of the leadframe, and to photoelectrically convert the received reflected light into an electric signal; and a cantilever assembly mounted on the measurement apparatus base so that a free end of the cantilever assembly is positioned to overhang the measurement stage, the cantilever assembly housing the distal end portion of the light source and the light receiver; and wherein the at least one processor executes instructions stored in the memory to: determine a reflection intensity value of the predetermined area on the surface of the leadframe based on the electric signal from the light receiver; and calculate a reflection ratio of the predetermined area on the surface of the leadframe based on the reflection intensity value and a predetermined reference reflection intensity value that is associated with the light source and that is stored in the memory.

In another example, a method of manufacturing a packaged device includes: irradiating light having a single predetermined wavelength on a predetermined area on a surface of a leadframe to determine whether a brightness ratio of the predetermined area is higher than a predetermined minimum brightness ratio threshold; mounting a semiconductor chip on the leadframe responsive to a determination that the brightness ratio is higher than the threshold; electrically connecting pads on the semiconductor chip with pads on the leadframe; applying a molding compound on the semiconductor chip and the leadframe and curing the molding compound; and singulating each of a plurality of the leadframes of a leadframe sheet to manufacture a plurality of packaged devices.

BRIEF DESCRIPTION OF THE DRAWINGS

For a detailed description of various examples, reference will now be made to the accompanying drawings in which.

DETAILED DESCRIPTION

This disclosure pertains to a method of measuring brightness of a surface of a leadframe by irradiating light having a single wavelength. As used herein, single wavelength light means light having a single wavelength. For example, the single wavelength light can be any of: red light having a single wavelength within the wavelength range of 620-750 nanometers (nm); green light having a single wavelength within the wavelength range of 495-570 nm; and blue light having a single wavelength within the wavelength range of 450-495 nm. In some examples, the single wavelength light is emitted by a light emitting diode (LED). That is, instead of utilizing full visible wavelength to characterize color of the leadframe surface, this disclosure proposes irradiating the leadframe surface with only a single predetermined wavelength and detecting reflection intensity of the leadframe surface responsive to the incident single wavelength light. For example, the reflection intensity represents a value of light power output for reflection light at a particular wavelength and detected by an optical sensor. The reflection intensity value can then be divided by a reflection intensity value of a standard known calibration piece to determine a reflection ratio. In some examples, a determination of whether to accept or reject the leadframe for further manufacturing operations is made based on the reflection ratio. More specifically, prior to measuring brightness of a target leadframe, an optical sensor of a leadframe surface measurement apparatus is calibrated by irradiating light having the single wavelength from a light source onto a standard calibration piece. In some examples, the standard calibration piece is coated with a noble metal such as gold or silver and represents peak brightness (reflection intensity) associated with the single wavelength light source. Reflected light received from the standard calibration piece is received by a light receiver (e.g., photodiode) that photoelectrically converts intensity of the reflected light into an electric signal. A processor then converts the electric signal into a digital value and stores the digital value as a predetermined reference reflection intensity value in memory. In some examples, the target leadframe surface is then irradiated with the light having the single wavelength and the reflected light from the leadframe surface is converted similarly to the reflected light from the standard calibration piece. A reflection ratio is determined based on the reflection intensity value of the leadframe surface and the predetermined reference reflection intensity value.

A determination regarding the leadframe surface being too dark or too bright is made based on the reflection ratio and predetermined minimum/maximum brightness ratio thresholds, thereby effectively performing incoming leadframe sheet quality control and preventing failure of subsequently performed pattern recognition processes that are based on measurement of leadframe surface brightness and color. In some examples, light irradiated from the light source is pulsed light and the light receiver is synchronized to receive the reflected light only during the time period of emission of pulsed light by the light source. Thus, the light receiver only recognizes the emitting frequency of the single wavelength incident light and eliminates ambient light as background noise. Further, by calibrating intensity of light emitted from the light source and using light having the single wavelength, wavelength variation is eliminated and the same lighting condition is used for each leadframe brightness measurement.

Figure 1A:
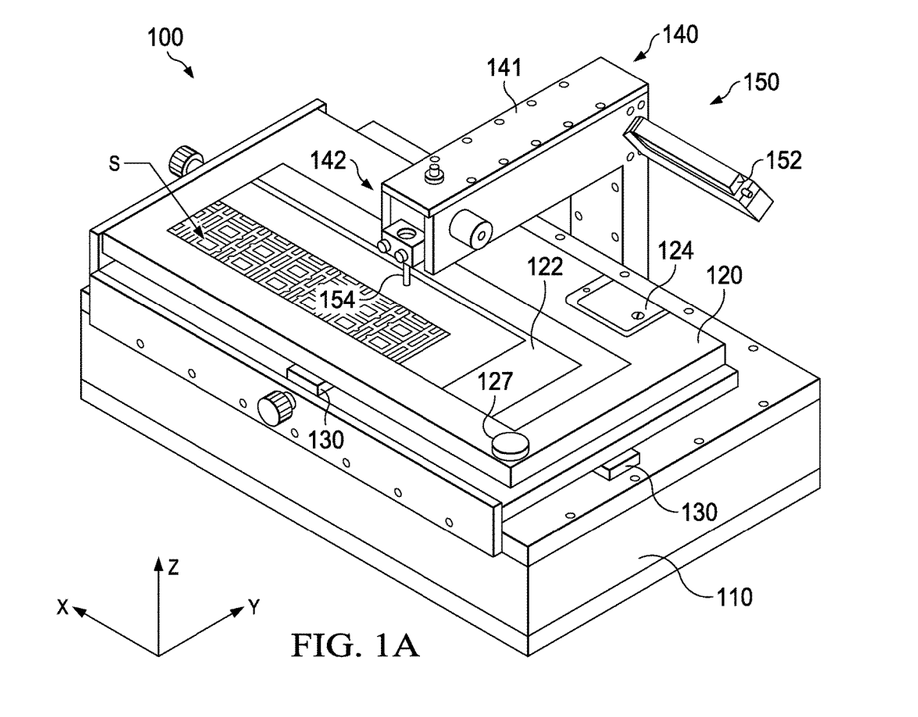
FIG. 1A shows a perspective view of leadframe surface measurement apparatus 100 according to one or more embodiments.

FIG. 1A shows a perspective view of leadframe surface measurement apparatus 100 according to one or more embodiments. In some examples, leadframe surface measurement apparatus 100 is configured as an integrated measurement jig having base 110 which movably supports measurement stage 120. Measurement stage 120 is supported on base 110 by one or more guide rails 130 to enable mechanical movement of stage 120 relative to base 110. In some examples, stage 120 is coupled to an XY-motor (not shown in FIG. 1A; see FIG. 3) and a Z-motor (not shown in FIG. 1A; see FIG. 3) to enable movement of stage in X-, Y-, and Z-directions along three orthogonal axes. Each of the XY-motor and the Z-motor is disposed between stage 120 and base 110 and is a linear motor or a rotary motor such as a servomotor or stepping motor to control movement of measurement stage 120. The motors are powered through power supply provided inside base 110 to position measurement stage 120 at a desired position in X-, Y-, and Z-directions.

Stage 120 includes sample tray 122, standard calibration piece 124, and knob 127 that secures sample tray 122 onto stage 120 by screwing onto a shaft extending from sample tray 122. Sample tray 122 securely holds leadframe sheet S that is an electrically conductive sheet (made of a metal such as copper) with a plurality of integrally formed leadframes whose brightness is to be measured by measurement apparatus 100. In one embodiment, sample tray 122 and knob 127 are excluded and leadframe sheet S is directly mounted on stage 120 for brightness measurement by measurement apparatus 100.

Standard calibration piece 124 is also secured to stage 120. Standard calibration piece 124 has a metallic (mirror) coating that has very high reflectivity. For example, standard calibration piece 124 has a coating of a noble metal such as gold, silver or aluminum or an alloy thereof. In one embodiment, standard calibration piece 124 is coated with silver that has known reflectivity of greater than 98% when irradiated with light having a wavelength in the range of 0.5 to 0.8 microns. By irradiating standard calibration piece 124 coated with protected silver with single wavelength light of approximately 630 nm, 98% absolute reflection will be achieved. As will be described in greater detail later, a reflection intensity of standard calibration piece 124 is recorded using measurement apparatus 100, thereby calibrating maximum reflection light intensity on a known reflection standard for measurement apparatus 100. Reflectivity of leadframe sheet S is then compared to this known piece.

Leadframe surface measurement apparatus 100 of FIG. 1A further includes cantilever assembly 140 and optical sensor 150. As shown in FIG. 1A, cantilever assembly 140 is mounted on base 110 of measurement apparatus 100 so that free end 142 of cantilever assembly 140 is positioned to overhang measurement stage 120. Free end 142 of cantilever assembly 140 houses distal end portions of a light source and a light receiver (not shown in FIG. 1A; see FIG. 3) of optical sensor 150 to irradiate a predetermined area of a surface of a leadframe of leadframe sheet S with light from the light source, and to receive reflected light from the surface of the leadframe of leadframe sheet S with the distal end portion of the light receiver at free end 142 of cantilever assembly 140. As shown in the example of FIG. 1A, optical sensor 150 is mounted on cantilever assembly 140. Alternately, optical sensor 150 is housed inside or mounted on base 110, or may be provided separately from base 110 and cantilever assembly 140. Optical sensor 150 is a fiber optic sensor, photoelectric sensor, laser sensor, and the like.

One set of one or more optical fiber cores is optically coupled at a proximal end thereof to the light source housed inside sensor body 152 of optical sensor 150 and coupled at a distal end thereof to lens 154 provided at free end 142 of cantilever assembly 140 to guide light from the light source to lens 154. Another set of one or more optical fiber cores is further provided to be optically coupled at a proximal end thereof to a light receiver housed inside sensor body 152 of optical sensor 150 and coupled at a distal end thereof to lens 154 to guide reflection light from the leadframe surface to the light receiver. Thus, both sets of one or more optical fiber cores extend from sensor body 152 over laterally extending portion 141 of cantilever assembly 140 to be optically coupled to lens 154 at free end 142.

The light source of optical sensor 150 emits light having a single predetermined wavelength for leadframe surface brightness measurement. The light source is an LED, a halogen lamp, a laser light source and the like. For example, the light source is an LED emitting red light at a single wavelength of approximately 630 nanometers (nm). Alternately, the light source is an LED emitting blue or green single wavelength light. Wavelength of light emitted from the light source for brightness measurement depends on the light wavelength that is used for pattern recognition in subsequent steps of the package assembly process.

In some examples, the light source of optical sensor 150 emits pulsed light at periodic, random or irregular intervals. A time period of emission of the pulse light of the light source of optical sensor 150 is less than a second. The light receiver of optical sensor 150 receives reflected light corresponding to only the single wavelength light emitted by the light source. For example, the light receiver is a photodiode that photoelectrically converts received reflected light into an electric signal. Light reception by the light receiver of optical sensor 150 is synchronized with the pulsed light emission by the light source so that the light receiver operates to receive reflected light only during the interval when the light source emits the single wavelength light. Thus, when the light source emits the single wavelength light during a first time period and ceases the emission during a second time period following the first time period, operation of the light receiver is synchronized so that the light receiver operates to receive reflected light only during the first time period but not during the second time period. Synchronizing light reception as described above results in optical sensor 150 emitting light at a certain frequency and the light receiver detecting only the reflected light having the same frequency as the emitted light and not detecting other light which may be background light or noise. This results in background light not affecting reading of the reflection light and elimination of background noise. As a result, brightness measurement accuracy of measurement apparatus 100 is improved.

Figure 1B:
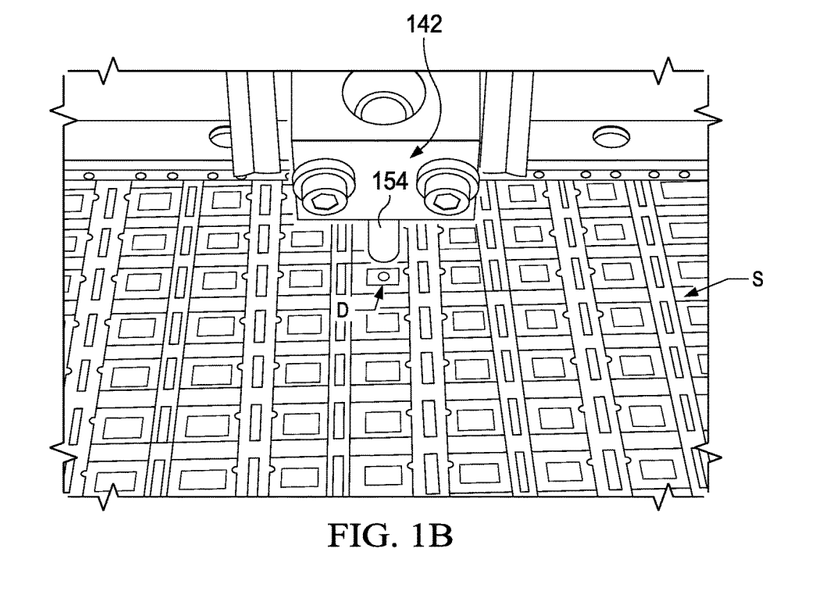
FIG. 1B shows an enlarged perspective view of a light irradiation operation conducted by leadframe surface measurement apparatus 100 according to one or more embodiments.

FIG. 1B shows an enlarged perspective view of light irradiation operation conducted by leadframe surface measurement apparatus 100 according to one or more embodiments. As shown in FIG. 1B, light is emitted from the distal end portion of the light source of optical sensor 150 at free end 142 of cantilever assembly 140. Lens 154 is provided at free end 142 of cantilever assembly 140 so as to be positioned on an optical path between the distal end portion of the light source and a surface of one of the leadframes of leadframe sheet S mounted on sample tray 122 of measurement apparatus 100. Single wavelength light emitted from the light source of optical sensor 150 passes through lens 154 and is irradiated on the leadframe surface of sheet S and reflected light from the leadframe surface of sheet S is again transmitted through lens 154 to be incident on the distal end portion of the light receiver of optical sensor 150. Lens 154 acts as a focus lens to reduce a beam size (spot size) of light emitted from the optical fiber core of the light source at the distal end portion thereof to focus the light onto a predetermined area on a surface of one of the leadframes of leadframe sheet S.

For example, as shown in FIG. 1B, the predetermined area is within a roughly rectangular area of die stage D on an upper surface of the leadframe where a semiconductor chip is to be mounted, with a plurality of leads of the leadframe being arranged outside of the area of die stage D and being electrically connected with electrodes of the semiconductor chip. In one embodiment, the predetermined area is at a center of die stage D. Stage 120 is adjusted in the X-, Y-, and Z-directions using the XY- and Z-motors to position the predetermined area on the surface of the leadframe on an optical axis of lens 154 to irradiate the predetermined area. In one embodiment, stage 120 is adjusted in the Z-direction to keep a focus distance between a lower surface of lens 154 and upper surface of the leadframe to 7 millimeters (mm) and lens 154 is adjusted to reduce the spot size of the irradiation light to 0.4 millimeters while the light source of optical sensor 150 emits red LED light at approximately 630 nm. In general, to ensure proper measurement of brightness of the surface of the leadframe, lens 154 is operated to adjust the spot size of emitted light so that the spot size is smaller than the area of die stage D of the leadframe of leadframe sheet S.

Figure 2:
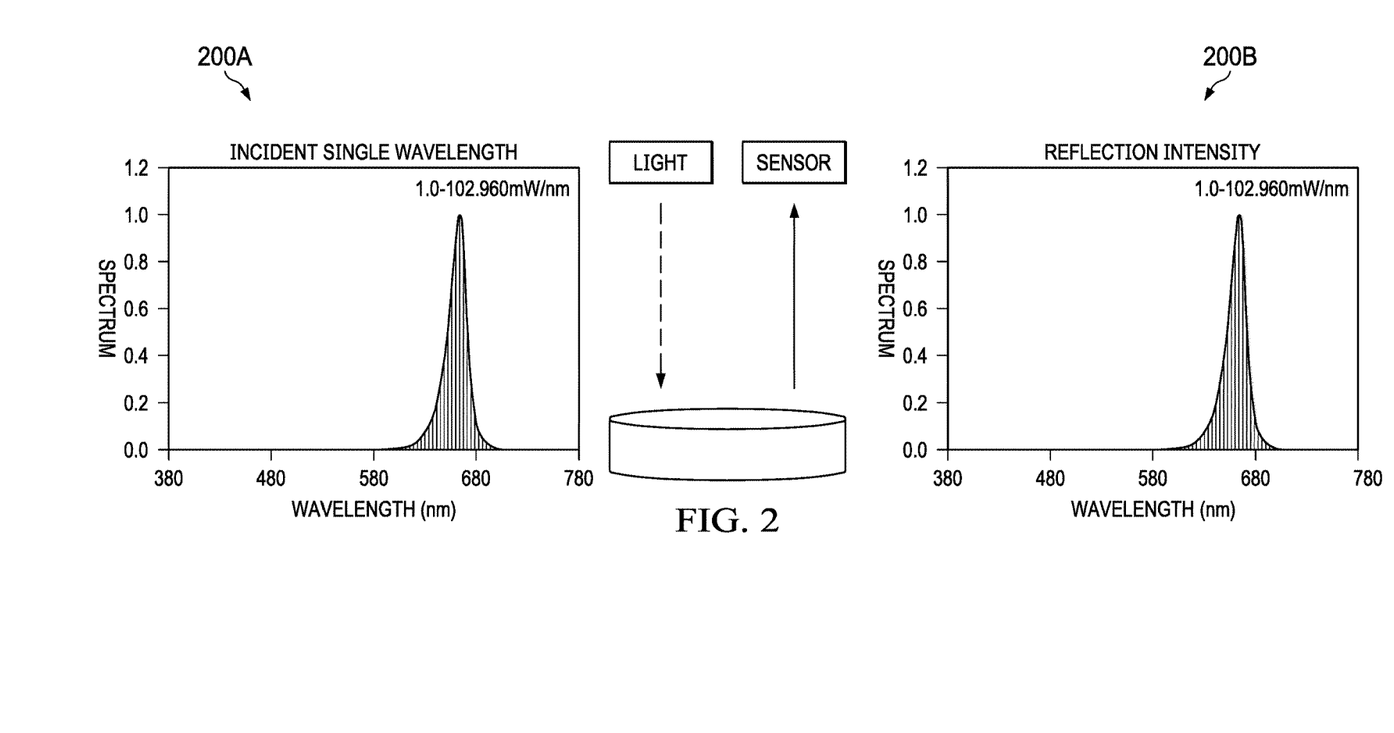
FIG. 2 shows graph 200A of an incident single wavelength and graph 200B of reflection intensity according to one or more embodiments.

Reflected light from the surface of the leadframe is received by the light receiver of optical sensor 150 to measure a reflection intensity (brightness) value of the received light. FIG. 2 shows graph 200A of an incident single wavelength and graph 200B of reflection intensity according to one or more embodiments. Abscissa in each of graphs 200A and 200B represents wavelength (nm) of incident or reflection light and ordinate represents a normalized power spectrum (milliwatt (mW)) indicating light power output at a particular wavelength for incident or reflection light.

As shown in graph 200A when red light having a single predetermined wavelength of approximately 630 nm is emitted from the light source of optical sensor 150, the light power output at the peak wavelength is 102.960 mW, which is equated to 1.0 on the normalized spectrum on the Y-axis. When this light having the single wavelength and power output characteristics as illustrated in incident single wavelength graph 200A is incident on the predetermined area of the leadframe surface of leadframe sheet S, the light receiver of optical sensor 150 detects reflection light having wavelength and power output characteristics as illustrated in graph 200B shown in FIG. 2.

As shown in graph 200B, the reflection light will have a certain amount of loss compared to the incident single wavelength light due to leadframe surface roughness, and as a result, intensity of the reflected light will be lower than the incident light. The light power output on the normalized spectrum for the reflected light is approximately 0.6 on the Y-axis as illustrated in reflection intensity graph 200B. In one embodiment, light receiver of optical sensor 150 photoelectrically converts reflected light received by a photodiode into an electric signal. The optical sensor 150 or a processor (see FIG. 3) further converts the electric signal into a digital value (reflection intensity value or normalized spectrum value). By comparing the normalized spectrum value corresponding to standard calibration piece 124 with the normalized spectrum value of the predetermined area of the target leadframe surface of leadframe sheet S, brightness of the leadframe surface is accurately measured so that subtle variations of the color and brightness of leadframe surfaces can be quantified with good repeatability and reproducibility.

Figure 3:
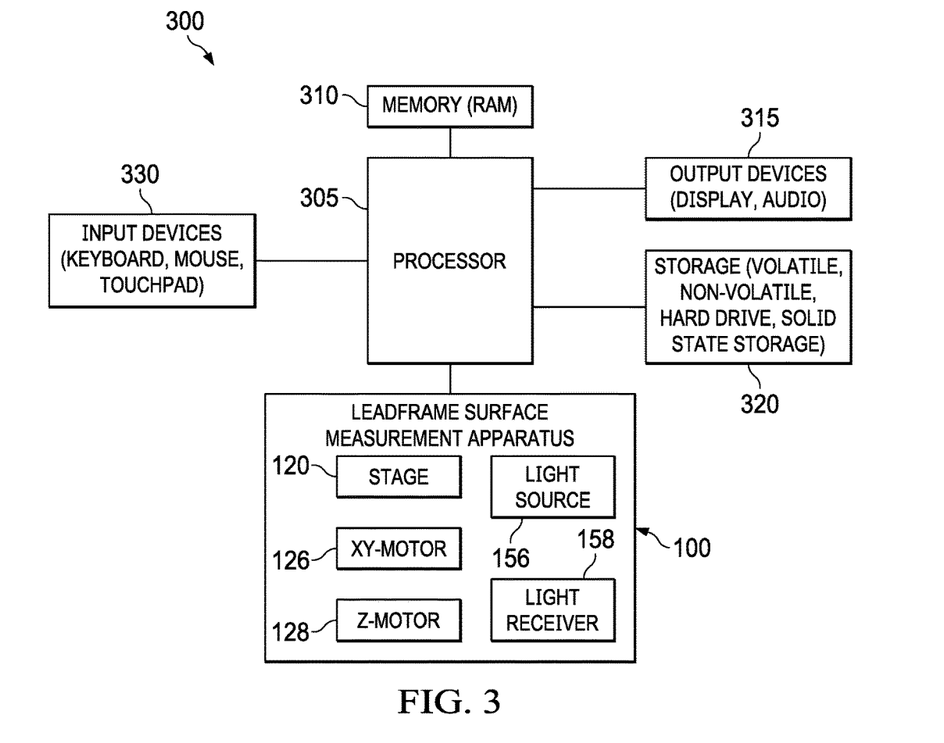
FIG. 3 shows a block diagram of leadframe surface measurement system 300 according to one or more embodiments.

FIG. 3 shows a high-level block diagram of leadframe surface measurement system 300 that is used to implement one or more disclosed embodiments. Only relevant portions of leadframe surface measurement system 300 are illustrated in FIG. 3. Further, detailed description of components of leadframe surface measurement system 300 that have been already described in detail in connection with leadframe surface measurement apparatus 100 of FIG. 1A is omitted here. Leadframe surface measurement system 300 includes leadframe surface measurement apparatus 100 (see FIG. 1A) which includes measurement stage 120, XY-motor 126, Z-motor 128, light source 156, and light receiver 158. Leadframe surface measurement system 300 further includes one or more input devices 330, such as a keyboard, mouse, or touchpad and one or more output devices 315, such as displays, or speakers for audio. Some devices may be configured as input/output devices as well (e.g., a network interface or touchscreen display).

As illustrated in the example of FIG. 3, leadframe surface measurement system 300 includes processor 305 that contains one or more hardware processors, where each hardware processor has a single or multiple processor cores. In one embodiment, the processor 305 includes at least one shared cache that stores data (e.g., computing instructions) that are utilized by one or more other components of processor 305. For example, the shared cache is a locally cached data stored in a memory for faster access by components of the processing elements that make up processor 305. Examples of processors include, but are not limited to a central processing unit (CPU) a microprocessor.

FIG. 3 illustrates that memory 310 is operatively and communicatively coupled to processor 305. Memory 310 is a non-transitory medium configured to store various types of data. For example, memory 310 includes one or more storage devices 320 that comprise a non-volatile storage device and/or volatile memory. Volatile memory, such as random access memory (RAM), can be any suitable non-permanent storage device. The non-volatile storage devices 320 can include one or more disk drives, optical drives, solid-state drives (SSDs), tap drives, flash memory, read only memory (ROM), and/or any other type memory designed to maintain data for a duration time after a power loss or shut down operation. In certain instances, the non-volatile storage devices 320 are used to store overflow data if allocated RAM is not large enough to hold all working data. The non-volatile storage devices 320 are also used to store programs that are loaded into the RAM when such programs are selected for execution.

Software programs may be developed, encoded, and compiled in a variety of computing languages for a variety of software platforms and/or operating systems and subsequently loaded and executed by processor 305. In one embodiment, the compiling process of the software program may transform program code written in a programming language to another computer language such that the processor 305 is able to execute the programming code. For example, the compiling process of the software program may generate an executable program that provides encoded instructions (e.g., machine code instructions) for processor 305 to accomplish specific, non-generic, particular computing functions.

After the compiling process, the encoded instructions may then be loaded as computer executable instructions or process steps to processor 305 from storage 320, from memory 310, and/or embedded within processor 305 (e.g., via a cache or on-board ROM). Processor 305 is configured to execute the stored instructions or process steps in order to perform instructions or process steps to transform the computing device into a non-generic, particular, specially programmed machine or apparatus. Stored data, e.g., data stored by a storage device 320, is accessed by processor 305 during the execution of computer executable instructions or process steps to instruct and operate one or more components within the leadframe surface measurement system 300.

A user interface (e.g., output devices 315 and input devices 330) can include a display, positional input device (such as a mouse, touchpad, touchscreen, or the like), keyboard, or other forms of user input and output devices. The user interface components are communicatively coupled to processor 305. When the output device is or includes a display, the display can be implemented in various ways, including by a liquid crystal display (LCD) or a cathode-ray tube (CRT) or light emitting diode (LED) display, such as an OLED display. In some examples, leadframe surface measurement system 300 comprises other components well known in the art, such as sensors, powers sources, and/or analog-to-digital converters, not explicitly shown in FIG. 3. One or more of processors 305, input devices 330, output devices 315, memory 310 and storage 320 are provided within leadframe surface measurement apparatus 100 or may be communicatively coupled to leadframe surface measurement apparatus 100 over a network.

Figure 4:
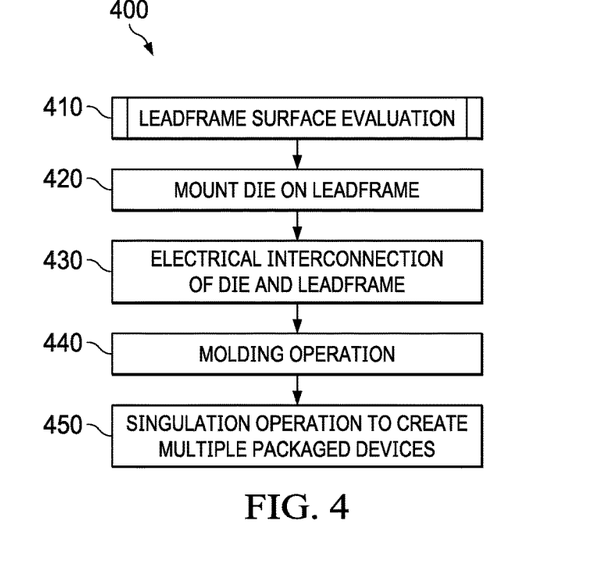
FIG. 4 shows flowchart 400 of a method of manufacturing a packaged device using leadframe surface measurement system 300 according to one or more embodiments.

FIG. 4 shows flowchart 400 of a method of manufacturing a packaged device using leadframe surface measurement system 300 according to one or more embodiments. Flowchart 400 begins at block 410 with processor 305 conducting leadframe surface evaluation to measure brightness of a leadframe surface of leadframe sheet S. Operations performed at block 410 are described in detail below in connection with flowchart 500 of FIG. 5.

At block 420, semiconductor chips (dies) are individually mounted on each die stage D of each leadframe of leadframe sheet S responsive to a determination at block 410 that the brightness of the leadframe surface is acceptable for a further semiconductor chip package assembly operation. At block 430, a wire bonding process of attaching each die to a corresponding leadframe on sheet S is performed by electrically connecting connection pads on the die with pads on the leadframe with, for example, copper wires. Connecting the die to the leadframe brings connections of the die to an outer area of the leadframe, thereby making it easier to solder the die and leadframe structure onto a circuit board. At block 440, a molding operation of applying a mold compound over the die and leadframe structure is performed. In one embodiment, the mold compound is applied on the die and leadframe structure and the compound is cured using thermal or ultraviolet radiation so as to harden and protect the die. Tips of the leadframe remain exposed after the curing to enable the resulting chip to be soldered onto a circuit board. Finally, at block 450, the molded and electrically connected packages of dies and leadframes on leadframe sheet S are singulated (separated) into individual packaged devices. In one embodiment, the semiconductor chip packages may be singulated using a saw or laser.

Figure 5:
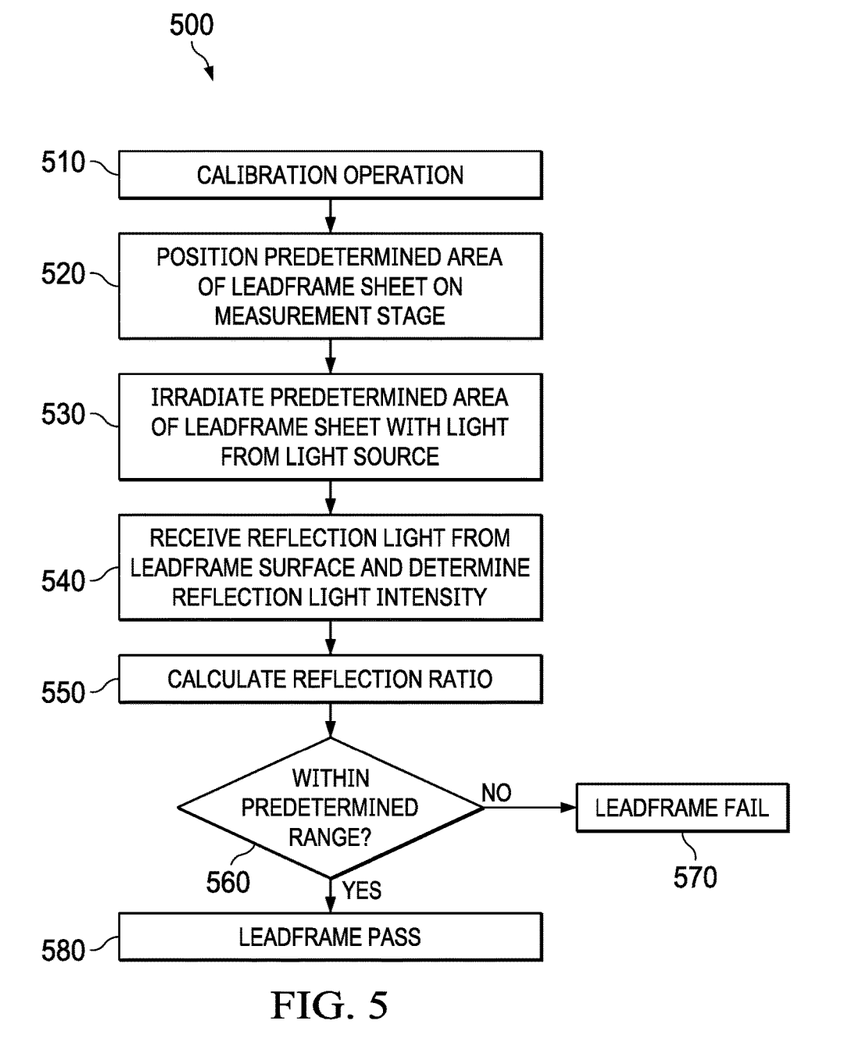
FIG. 5 shows flowchart 500 of a method of evaluating a leadframe surface according to one or more embodiments.

FIG. 5 shows flowchart 500 of a method of evaluating a leadframe surface corresponding to block 410 of flowchart 400 according to one or more embodiments. Flowchart 500 begins at block 510 with processor 305 conducting a calibration operation of measurement apparatus 100 with standard calibration piece 124. Processor 305 accesses programs and data stored in storage 320 to perform the calibration operation. For example, processor 305 obtains XYZ position information of standard calibration piece 124 mounted on measurement stage 120 and execute instructions to operate XY-motor 126 and Z-motor 128 to position standard calibration piece 124 on an optical axis of lens 154 for brightness measurement and calibration. Processor 305 then executes instructions to control operations of light source 156 and light receiver 158 to irradiate standard calibration piece 124 with single wavelength light and obtain reflection light. Processor 305 further controls operations of light source 156 and light receiver 158 to irradiate the single wavelength light as a pulsed light and synchronize operation of light receiver 158 with the pulsed light emission of light source 156 to eliminate effects of background light, thereby obtaining a more accurate brightness measurement value standard calibration piece 124. In some examples, processor 305 then operates an analog-to-digital converter (now shown) to convert the electric signal obtained from light receiver 158 into a digital value and store the digital value as a predetermined reference reflection intensity value in storage 320. In some examples, calibration operation at block 510 is performed only once when apparatus 100 is powered ON for brightness measurement. Actual brightness measurement operation for one or more leadframe surfaces on one or more sheets S is then performed once the apparatus 100 has been calibrated at block 510.

At block 520, processor 305 obtains XYZ position information of a predetermined area on a leadframe surface of leadframe sheet S mounted on sample tray 122 that is to be subject to the brightness measurement operation. Processor 305 executes instructions to operate XY-motor 126 and Z-motor 128 to position the predetermined area on the optical axis of lens 154 for brightness measurement.

At block 530, processor 305 controls light source 156 to irradiate single wavelength light onto the predetermined area on the leadframe surface of sheet S, and at block 540, processor 305 controls light receiver 158 to receive reflected light corresponding to the single wavelength light incident on the predetermined area on the surface of the leadframe of leadframe sheet S. Processor 305 further controls operations of light source 156 and light receiver 158 to irradiate the single wavelength light as a pulsed light and synchronizes operation of light receiver 158 with the pulsed light emission of light source 156 to eliminate effects of background light, thereby obtaining a more accurate brightness measurement value of the predetermined area of leadframe sheet S. In some examples, processor 305 then operates an analog-to-digital converter (now shown) to convert the electric signal obtained from light receiver 158 and corresponding to the reflection light intensity of the predetermined area of the surface of the leadframe of leadframe sheet S into a digital value and stores the digital value as a reflection intensity value in storage 320.

At block 550, processor 305 calculates a reflection ratio based on the stored reflection intensity value and the stored predetermined reference reflection intensity value. For example, processor 305 divides the reflection intensity value of target leadframe surface with the predetermined reference reflection intensity value of standard calibration piece 124 to calculate the reflection ratio. The value calculated at block 550 is expressed in percentage form (i.e., 1% to 100%) or as a value representing a result of the division.

At block 560, processor 305 determines whether the calculated reflection ratio is within a predetermined permissible reflection ratio range. Information regarding the permissible reflection ratio range is stored in storage 320 and is predetermined for each type of leadframe sheet S whose brightness is to be measured with measurement apparatus 100. For example, a leadframe brightness is considered permissible if the reflection intensity value of the leadframe surface is more than 10% of the stored predetermined reference reflection intensity value of standard calibration piece 124. Thus, if the calculated reflection ratio is lower than a minimum brightness ratio threshold ("NO" at block 560), processor 305 determines that the leadframe surface is too dark and therefore, the leadframe is unusable for subsequent semiconductor package assembly operations (block 570). Conversely, if the calculated reflection ratio is higher than a maximum brightness ratio threshold ("NO" at block 560), processor 305 determines that the leadframe surface is too bright and therefore, the leadframe is unusable for subsequent semiconductor package assembly operations (block 570). In some examples, processor 305 indicates the leadframe is unacceptable for a manufacturing operation at block 570 by displaying a result of the determination at block 560 on a display.

If, on the other hand, processor 305 determines that the calculated reflection ratio is within the predetermined permissible reflection ratio range ("YES" at block 560), processor 305 determines that the leadframe surface brightness is within an acceptable operating range, and therefore, the leadframe is usable for subsequent semiconductor package assembly operations (block 580). In some examples, processor 305 indicates the leadframe is acceptable for a manufacturing operation at block 580 by displaying a result of the determination at block 560 on a display. In one embodiment, processor 305 executes instructions stored in storage 320 to perform the steps of the leadframe surface evaluation method illustrated in flowchart 500 of FIG. 5 automatically, without any operation by a user. Thus, for example, processor 305 automatically controls operations of one or more of stage 120, XY-motor 126, Z-motor 128, light source 156, and/or light receiver 158 to perform the calibration and brightness measurement operations. Processor 305 then automatically outputs a result of the brightness measurement operation to a user by, for example, displaying a result on a display 315 or an audible signal. Alternatively, one or more of the operations of flowchart 500 are performed manually. In one embodiment, the operations of flowchart 500 of FIG. 5 can be used in in-line monitoring of an assembly line of a die bonder. Brightness can then be measured at the predetermined area of the surface of each leadframe for quick inspection and "pass" or "fail" determination.

Experiments have been conducted to test viability of the leadframe surface brightness measurement method based on single wavelength reflection according to the present disclosure. A Six Sigma Gage Repeatability and Reproducibility (GRR) study was performed to assess the leadframe surface brightness measurement method according to the present disclosure by measuring the amount of variation in the measurement system arising from sources like particular measurement apparatus used or personnel taking the measurement. The results showed that the overall GRR for the leadframe surface brightness measurement method according to the present disclosure was less than 10% with fast examination time (e.g., measurement time of less than one second per measurement).

Figure 6:
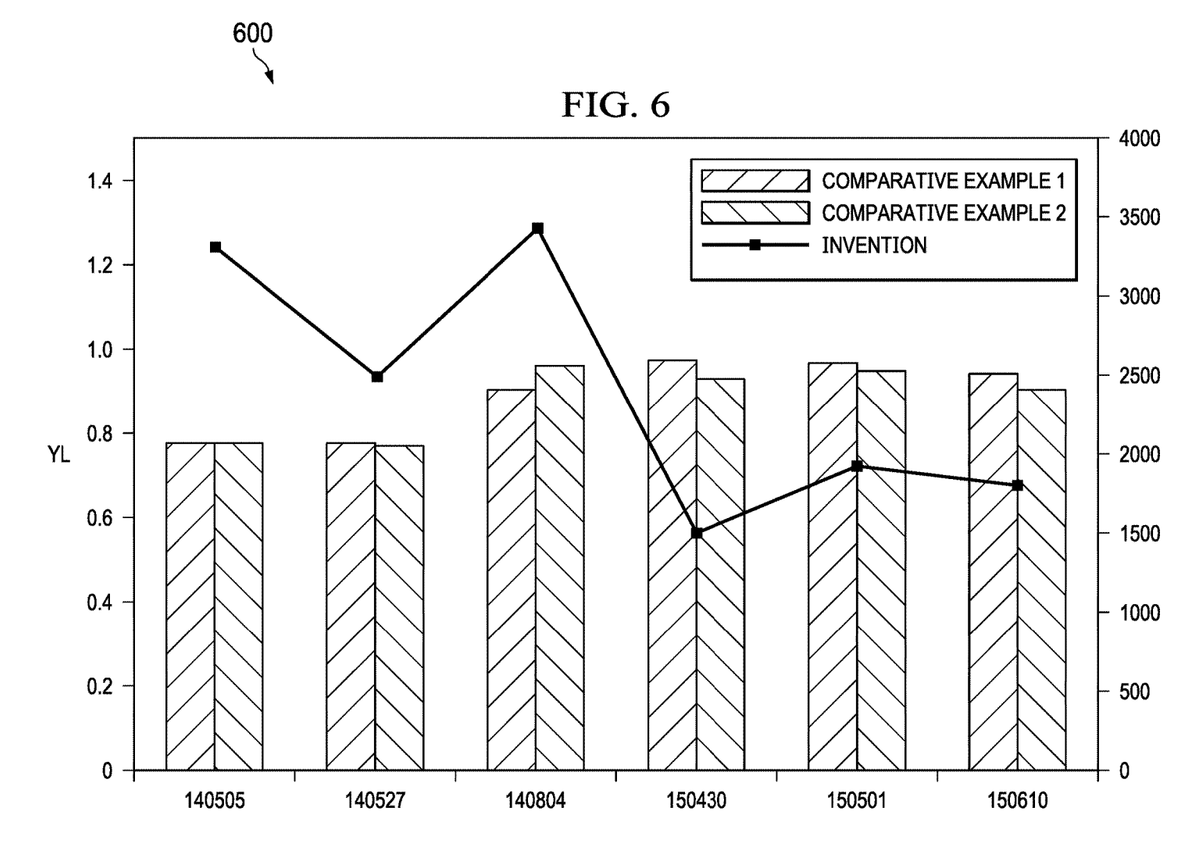
FIG. 6 shows graph 600 showing comparison between brightness measurement according to leadframe surface brightness measurement method based on single wavelength reflection according to one or more embodiments of the present disclosure and brightness measurement according to Comparative Examples 1 and 2 in which the brightness was measured using conventional techniques.

Conventional techniques for measuring and quantifying variations in leadframe surface brightness and color include mean grayscale value calculation method and XYZ tristimulus measurement method. In the mean grayscale value calculation method an image of a leadframe surface taken under a microscope with fixed light intensity is cropped to focus on a leadframe die stage surface area, the cropped image is analyzed to generate a histogram of the cropped area and mean grayscale value is calculated for the cropped area based on the histogram to determine a mean brightness value of the leadframe surface. In the XYZ tristimulus method, a halogen lamp is used as a light source to detect reflection in multiple wavelengths in a wavelength range of 380 nm-780 nm. Reflection spectrum R(λ) is converted to XYZ by x(λ), y(λ), z(λ) color matching functions and X, Y, Z values can be judged as red/green/blue reflection intensity values to detect a color of the leadframe surface in unit GAM. However, with the conventional mean grayscale value calculation method, background lighting introduces too much variation in the mean grayscale calculation thereby lowering reliability and reproducibility of measured grayscale values. Further, with the XYZ tristimulus method, brightness measurement for a roughened leadframe surface is not very consistent and is susceptible to various hardware and software variations and therefore not feasible. Inventors of the present application conducted experiments on different batches of leadframe sheets having the same specifications received over an extended period of time and determined that the leadframe surface brightness measurement method based on single wavelength reflection according to the present disclosure has better correlation to visual appearance (brightness) of the leadframe surface than the above described conventional techniques. As shown in graph 600 of FIG. 6, brightness measurement according to the leadframe surface brightness measurement method based on single wavelength reflection according to the present disclosure has better correlation to actual leadframe surface brightness than measurement according to Comparative Examples 1 and 2 using conventional techniques involving color measurement based on measured RGB reflection values using XYZ tristimulus method or mean grayscale calculation method.

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors. The recitation "approximately" before the recitation of a value is intended to cover all values within the range of ±10% of the value.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of manufacturing a packaged device, the method comprising:
   irradiating light having a single predetermined wavelength on a predetermined area on a surface of a leadframe to determine whether a brightness ratio of the predetermined area is higher than a predetermined minimum brightness ratio threshold;
   mounting a semiconductor chip on the leadframe responsive to a determination that the brightness ratio of the predetermined area is higher than the threshold;
   electrically connecting pads on the semiconductor chip with pads on the leadframe;
   applying a molding compound on the semiconductor chip and the leadframe and curing the molding compound; and
   singulating each of a plurality of the leadframes of a leadframe sheet to manufacture a plurality of packaged devices.

2. The method of manufacturing the packaged device according to claim 1, further comprising:
   positioning the leadframe on a measurement apparatus at a first predetermined distance relative to an end portion of a light source of an optical sensor;
   irradiating the predetermined area on the surface of the leadframe with the light having the single predetermined wavelength from the light source;
   receiving, with a light receiver of the optical sensor, reflected light from the predetermined area on the surface of the leadframe, and converting the reflected light into an electric signal;
   determining a reflection intensity value of the predetermined area on the surface of the leadframe based on the electric signal; and
   calculating a reflection ratio of the predetermined area on the surface of the leadframe based on the reflection intensity value and a predetermined reference reflection intensity value associated with the light source.

3. The method of manufacturing the packaged device according to claim 2, further comprising:
   positioning a calibration piece on the measurement apparatus and irradiating the calibration piece with the light having the single predetermined wavelength;
   receiving, with the light receiver of the optical sensor, reflected light from the calibration piece;

determining the predetermined reference reflection intensity value based on the reflected light from the calibration piece; and dividing the reflection intensity value by the predetermined reference reflection intensity value to calculate the reflection ratio.

4. The method of manufacturing the packaged device according to claim 3, wherein the calibration piece is coated with one or more of gold, silver, and aluminum.

5. The method of manufacturing the packaged device according to claim 2, wherein the reflected light from the predetermined area on the surface of the leadframe represents a brightness of the surface of the leadframe; and wherein the method further comprises indicating the brightness of the surface of the leadframe as being within a permissible range when the reflection ratio is higher than a predetermined minimum brightness ratio threshold.

6. The method of manufacturing the packaged device according to claim 2, wherein the light source is a pulsed light source, and wherein the method further comprises:

irradiating the predetermined area on the surface of the leadframe with the light having the single predetermined wavelength during a first time period;

ceasing irradiating the predetermined area on the surface of the leadframe with the light having the single predetermined wavelength during a second time period following the first time period; and synchronizing an operation of the light receiver with an operation of the light source such that the light receiver operates to receive the reflected light during the first time period but not during the second time period.

7. The method of manufacturing the packaged device according to claim 6, wherein the light source is a pulsed light emitting diode (LED) that emits red light at 630 nanometers.

8. The method of manufacturing the packaged device according to claim 2, wherein the optical sensor is a fiber optic sensor, and wherein the light source comprises an LED and a first optical fiber guiding the light from the LED to the distal end portion of the light source, and wherein the light receiver comprises a photodiode and a second optical fiber guiding the reflected light from a distal end portion of the light receiver to the photodiode.

9. method of manufacturing the packaged device according to claim 2, further comprising:

positioning a lens in an optical path between the distal end portion of the light source and the predetermined area on the surface of the leadframe on the measurement apparatus; and adjusting a focus positon of the lens to focus the light from the light source on the predetermined area on the surface of the leadframe.

10. The method of manufacturing the packaged device according to claim 2, wherein the light receiver is a photodiode.

11. The method of manufacturing the packaged device according to claim 1, wherein the irradiating light is a red light having a single wavelength within the wavelength range of 620-750 nanometers (nm).

12. The method of manufacturing the packaged device according to claim 1, wherein the irradiating light is a green light having a single wavelength within the wavelength range of 495-570 nanometers (nm).

13. The method of manufacturing the packaged device according to claim 1, wherein the irradiating light is a blue light having a single wavelength within the wavelength range of 450-495 nanometers (nm).

14. A method of manufacturing packaged devices, the method comprising:

irradiating light having a single predetermined wavelength on a predetermined area on a surface of a leadframe in a leadframe sheet to determine whether a brightness ratio of the predetermined area is higher than a predetermined minimum brightness ratio threshold;

mounting a semiconductor chip on each leadframe in the leadframe sheet responsive to a determination that the brightness ratio of the predetermined area is higher than the threshold;

electrically connecting pads on each semiconductor chip with pads on the leadframe to which it is attached;

applying a molding compound on the semiconductor chips and the leadframe sheet and curing the molding compound; and singulating each of a plurality of the leadframes of a leadframe sheet to manufacture a plurality of packaged devices.

15. The method of manufacturing the packaged devices according to claim 14, further comprising:

positioning the leadframe sheet on a measurement apparatus at a first predetermined distance relative to an end portion of a light source of an optical sensor;

irradiating the predetermined area on the surface of the leadframe sheet with the light having the single predetermined wavelength from the light source;

receiving, with a light receiver of the optical sensor, reflected light from the predetermined area on the surface of the leadframe sheet, and converting the reflected light into an electric signal;

determining a reflection intensity value of the predetermined area on the surface of the leadframe sheet based on the electric signal; and calculating a reflection ratio of the predetermined area on the surface of the leadframe sheet based on the reflection intensity value and a predetermined reference reflection intensity value associated with the light source.

16. The method of manufacturing the packaged device according to claim 15, further comprising:

positioning a calibration piece on the measurement apparatus and irradiating the calibration piece with the light having the single predetermined wavelength;

receiving, with the light receiver of the optical sensor, reflected light from the calibration piece;

determining the predetermined reference reflection intensity value based on the reflected light from the calibration piece; and dividing the reflection intensity value by the predetermined reference reflection intensity value to calculate the reflection ratio.

17. The method of manufacturing the packaged device according to claim 16, wherein the calibration piece is coated with one or more of gold, silver, and aluminum.

18. The method of manufacturing the packaged device according to claim 15, wherein the reflected light from the predetermined area on the surface of the leadframe sheet represents a brightness of the surface of the leadframe sheet; and wherein the method further comprises indicating the brightness of the surface of the leadframe sheet as being within a permissible range when the reflection ratio is higher than a predetermined minimum brightness ratio threshold.

19. The method of manufacturing the packaged device according to claim 15, wherein the light source is a pulsed light source, and wherein the method further comprises:
   irradiating the predetermined area on the surface of the leadframe sheet with the light having the single predetermined wavelength during a first time period;
   ceasing irradiating the predetermined area on the surface of the leadframe sheet with the light having the single predetermined wavelength during a second time period following the first time period; and
   synchronizing an operation of the light receiver with an operation of the light source such that the light receiver operates to receive the reflected light during the first time period but not during the second time period.

20. The method of manufacturing the packaged device according to claim 19, wherein the light source is a pulsed light emitting diode (LED) that emits red light at 630 nanometers.

21. The method of manufacturing the packaged device according to claim 15, wherein the optical sensor is a fiber optic sensor, and wherein the light source comprises an LED and a first optical fiber guiding the light from the LED to the distal end portion of the light source, and wherein the light receiver comprises a photodiode and a second optical fiber guiding the reflected light from a distal end portion of the light receiver to the photodiode.

22. The method of manufacturing the packaged device according to claim 15, further comprising:
   positioning a lens in an optical path between the distal end portion of the light source and the predetermined area on the surface of the leadframe sheet on the measurement apparatus; and
   adjusting a focus positon of the lens to focus the light from the light source on the predetermined area on the surface of the leadframe sheet.

23. The method of manufacturing the packaged device according to claim 15, wherein the light receiver is a photodiode.

24. The method of manufacturing the packaged device according to claim 14, wherein the irradiating light is a red light having a single wavelength within the wavelength range of 620-750 nanometers (nm).

25. The method of manufacturing the packaged device according to claim 14, wherein the irradiating light is a green light having a single wavelength within the wavelength range of 495-570 nanometers (nm).

26. The method of manufacturing the packaged device according to claim 14, wherein the irradiating light is a blue light having a single wavelength within the wavelength range of 450-495 nanometers (nm).

27. A method of manufacturing a packaged device, the method comprising:
   irradiating light having a single predetermined wavelength on a predetermined area on a surface of a leadframe to determine whether a brightness ratio of the predetermined area is higher than a predetermined minimum brightness ratio threshold;
   mounting a semiconductor chip on the leadframe responsive to a determination that the brightness ratio of the predetermined area is higher than the threshold;
   electrically connecting pads on the semiconductor chip with pads on the leadframe;
   applying a molding compound on the semiconductor chip and the leadframe and curing the molding compound; and
   singulating the mold encapsulated semiconductor chip and lead frame from a leadframe sheet.

* * * * *